(12) United States Patent
Hoshi et al.

(10) Patent No.: US 9,845,761 B2
(45) Date of Patent: Dec. 19, 2017

(54) FUEL ESTIMATION APPARATUS

(71) Applicant: DENSO CORPORATION, Kariya, Aichi-pref. (JP)

(72) Inventors: Shinya Hoshi, Kariya (JP); Atsunori Okabayashi, Kariya (JP)

(73) Assignee: DENSO CORPORATION, Kariya (JP)

( * ) Notice: Subject to any disclaimer, the term of this patent is extended or adjusted under 35 U.S.C. 154(b) by 0 days.

(21) Appl. No.: 15/176,540

(22) Filed: Jun. 8, 2016

(65) Prior Publication Data

US 2016/0363084 A1    Dec. 15, 2016

(30) Foreign Application Priority Data

Jun. 11, 2015 (JP) ................... 2015-118593

(51) Int. Cl.
*F02D 41/26* (2006.01)
*F02D 41/14* (2006.01)
(Continued)

(52) U.S. Cl.
CPC ..... *F02D 41/3005* (2013.01); *F02D 19/0636* (2013.01); *F02D 35/02* (2013.01); *F02D 41/0025* (2013.01); *F02D 41/123* (2013.01); *F02D 41/1444* (2013.01); *F02D 41/26* (2013.01); *F02D 41/402* (2013.01); *G01N 33/2829* (2013.01); *F02B 1/12* (2013.01); *F02D 35/023* (2013.01); *F02D 35/025* (2013.01); *F02D 35/028* (2013.01); *F02D 41/144* (2013.01); *F02D 41/1454* (2013.01); *F02D 2200/0602* (2013.01);
(Continued)

(58) Field of Classification Search
CPC .............. F02D 41/3005; F02D 41/123; F02D 41/0025; F02D 41/26; F02D 41/1444; F02D 41/1454; F02D 41/402; F02D 35/02; F02D 35/023; F02D 35/025; F02D 35/028; F02D 2200/0602; F02D 2200/0612; F02D 19/0636; F02D 2250/38; G01N 33/2829; F02B 1/12
See application file for complete search history.

(56) References Cited

U.S. PATENT DOCUMENTS 4,594,979 A * 6/1986 Yasuhara .............. F02D 41/123
123/357
5,267,163 A * 11/1993 Yoshida .............. F02D 41/0025
123/1 A
(Continued)

FOREIGN PATENT DOCUMENTS

JP    2013-24138    2/2013

*Primary Examiner* — Hieu T Vo
*Assistant Examiner* — Arnold Castro
(74) *Attorney, Agent, or Firm* — Nixon & Vanderhye P.C.

(57) ABSTRACT

A fuel estimation apparatus includes a combustion characteristic acquisition portion and a mixing ratio estimation portion. The combustion characteristic acquisition portion acquiring a combustion characteristic value indicating a physical amount relating to a combustion of an internal combustion engine acquires the combustion characteristic values of the combustions executed in different combustion conditions. The mixing ratio estimation portion estimates the mixing ratios of various components included in a fuel, based on the combustion characteristic values acquired by the combustion characteristic acquisition portion.

9 Claims, 6 Drawing Sheets

(51) Int. Cl.

| | | |
|---|---|---|
| *F02D 41/30* | (2006.01) | |
| *F02D 41/40* | (2006.01) | |
| *G01N 33/28* | (2006.01) | |
| *F02D 41/12* | (2006.01) | |
| *F02D 19/06* | (2006.01) | |
| *F02D 35/02* | (2006.01) | |
| *F02D 41/00* | (2006.01) | |
| *F02B 1/12* | (2006.01) | |

(52) U.S. Cl.
CPC .. *F02D 2200/0612* (2013.01); *F02D 2250/38* (2013.01); *Y02T 10/44* (2013.01)

(56) References Cited

U.S. PATENT DOCUMENTS

| | | | | |
|---|---|---|---|---|
| 6,990,956 B2* | 1/2006 | Niimi | ................ | F02D 19/0628 123/1 A |
| 7,945,373 B2* | 5/2011 | Vestrini | ................ | F02D 19/0631 701/103 |
| 2006/0118085 A1* | 6/2006 | Oda | ................ | F02D 19/081 123/406.3 |
| 2007/0156322 A1* | 7/2007 | Soga | ................ | F02D 41/16 701/104 |
| 2009/0063005 A1* | 3/2009 | Streib | ................ | F02D 35/028 701/101 |
| 2010/0063708 A1* | 3/2010 | Dotzer | ................ | F02D 19/0628 701/102 |
| 2010/0312459 A1* | 12/2010 | Utsumi | ................ | F02D 15/02 701/106 |
| 2010/0326410 A1* | 12/2010 | Yeh | ................ | C10L 1/04 123/575 |
| 2011/0208408 A1* | 8/2011 | Haskara | ................ | F02D 35/023 701/105 |
| 2013/0289849 A1* | 10/2013 | Uehara | ................ | F02B 31/06 701/103 |
| 2014/0025277 A1* | 1/2014 | Masubuchi | ................ | F02D 15/04 701/104 |
| 2015/0252745 A1* | 9/2015 | Naruse | ................ | F02D 35/028 123/294 |
| 2015/0346180 A1* | 12/2015 | Yamada | ................ | F02D 41/28 701/105 |
| 2016/0097339 A1* | 4/2016 | Naruse | ................ | F02D 41/1467 123/435 |
| 2016/0290250 A1* | 10/2016 | Kurotani | ................ | F02D 19/0626 |
| 2016/0363074 A1* | 12/2016 | Hoshi | ................ | F02D 41/1454 |
| 2016/0363080 A1* | 12/2016 | Okabayashi | ................ | F02D 41/1438 |

* cited by examiner

FIG. 3

$$\begin{pmatrix} \text{MIXING AMOUNT OF NORMAL PARAFFIN TYPE} \\ \text{MIXING AMOUNT OF NAPHTHENIC TYPE} \\ \text{MIXING AMOUNT OF ISOPARAFFIN TYPE} \\ \text{MIXING AMOUNT OF AROMATIC TYPE} \\ \cdots \end{pmatrix} = \begin{pmatrix} a_{00} & \cdots & a_{0Y} \\ \vdots & \ddots & \vdots \\ a_{X0} & \cdots & a_{XY} \end{pmatrix} \times \begin{pmatrix} TD(i) \\ TD(j) \\ TD(k) \\ TD(l) \\ \cdots \end{pmatrix} \begin{matrix} : P(i), T(i), O_2(i), Pc(i) \\ : P(j), T(j), O_2(j), Pc(j) \\ : P(k), T(k), O_2(k), Pc(k) \\ : P(l), T(l), O_2(l), Pc(l) \end{matrix}$$

MOLECULAR STRUCTURE TYPE     CONSTANT     COMBUSTION PARAMETERS

FIG. 4
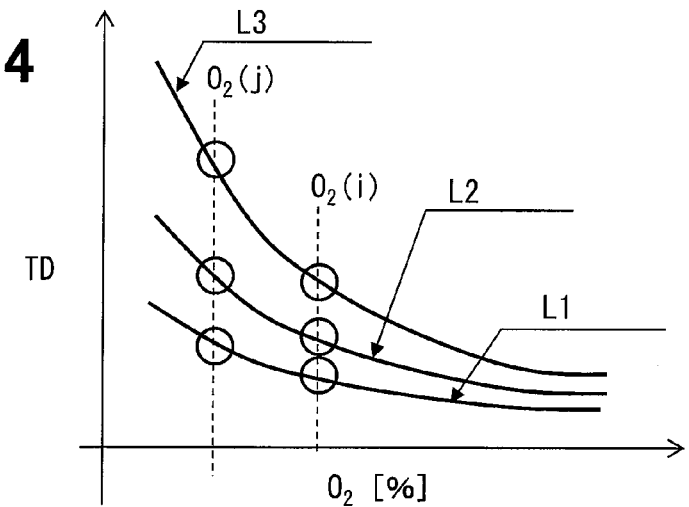
FIG. 5
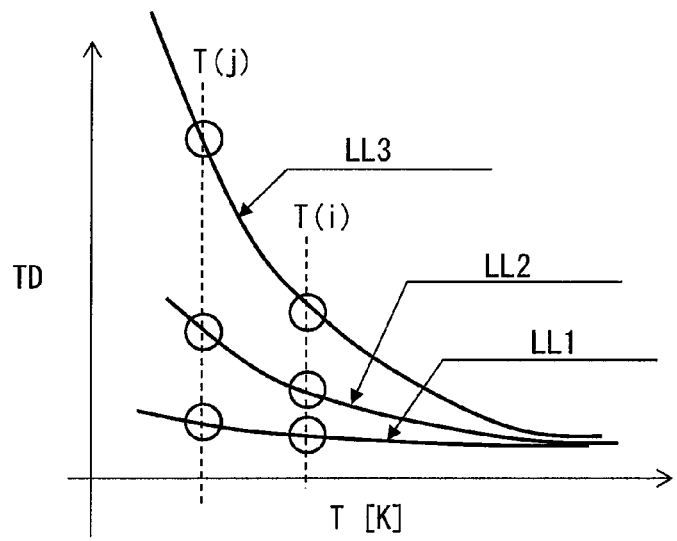
FIG. 6
|    | A     | B     | C     |
|----|-------|-------|-------|
| F1 | LARGE | LARGE | SMALL |
| F2 | SMALL | LARGE | SMALL |
| F3 | LARGE | SMALL | LARGE |

FUEL ESTIMATION APPARATUS

CROSS REFERENCE TO RELATED APPLICATION

This application is based on Japanese Patent Application No. 2015-118593 filed on Jun. 11, 2015, the disclosure of which is incorporated herein by reference.

TECHNICAL FIELD

The present disclosure relates to a fuel estimation apparatus relating to a fuel used in a combustion of an internal combustion engine.

BACKGROUND

A fuel supplied to a user has various characteristics, and an index indicating one of the characteristics is a cetane number that is equivalent to an ignitionability. When the fuel that the cetane number is low is supplied, the ignitionability is deteriorated. Therefore, a control object such as an injection time point of the fuel, an injection amount of the fuel, an injection pressure, and an EGR amount, is changed to be easily ignited.

According to JP2013-24138A, the cetane number is cor-relative to a fuel density. The fuel density is detected to estimate the cetane number, and the control object is changed according to an estimation result. Therefore, a non-combustion HC, a NOx, and a particulate matter (PM) which are included in an exhaust gas can be reduced, and a fuel consumption can be improved.

SUMMARY

However, it is known that components included in a fuel are different when the fuel differs, and a mixing ratio of each of the components differs when the fuel differs. Therefore, when the cetane numbers are the same and when the components actually included in the fuels are different from each other, the mixing ratios of the components differ. Thus, in a conventional control changing the control object according to the cetane number, there is a limit that the conventional control is optimally executed according to the fuel.

Recently, when a control of the internal combustion engine is changed to match the fuel supplied by the user, it is necessary to accurately acquire a fuel characteristic.

It is an object of the present disclosure to provide a fuel estimation apparatus which estimates mixing ratios of various components included in a fuel so as to accurately acquire a characteristic of the fuel.

According to an aspect of the present disclosure, the fuel estimation apparatus includes a combustion characteristic acquisition portion acquiring a combustion characteristic value indicating a physical amount relating to a combustion of an internal combustion engine, the combustion characteristic acquisition portion acquiring the combustion characteristic values of the combustions executed in different combustion conditions; and a mixing ratio estimation portion estimating the mixing ratios of various components included in a fuel, based on the combustion characteristic values acquired by the combustion characteristic acquisition portion.

When fuels used in the combustion are the same and when the combustion conditions such as the cylinder pressures or the cylinder temperatures are different from each other, the combustion characteristic values such as the ignition delay times or the heat generation amounts differ. Levels of variations of the combustion characteristic values relative to variations of the combustion conditions differ due to differences in fuel characteristics. According to the present disclosure, since the fuel estimation apparatus estimates the mixing ratios of the various components included in the fuel based on the combustion characteristic values detected in different combustion conditions, the fuel estimation apparatus can accurately acquire a fuel characteristic that is a characteristic of the fuel.

BRIEF DESCRIPTION OF THE DRAWINGS

The above and other objects, features and advantages of the present disclosure will become more apparent from the following detailed description made with reference to the accompanying drawings. In the drawings:

FIG. 3 is a diagram showing a relationship between plural ignition delay times, combustion parameters indicating easiness levels of combustions, and mixing mounts of various components;

FIG. 4 is a diagram showing a relationship between a characteristic line indicating a variation of the ignition delay time generated due to a cylinder oxygen concentration and a molecular structure type of a fuel;

FIG. 5 is a diagram showing a relationship between a characteristic line indicating a variation of the ignition delay time generated due to a cylinder temperature and the molecular structure type of the fuel;

FIG. 6 is a diagram showing a relationship between the characteristic line specified based on the ignition delay time and a mixing ratio of the molecular structure type;

DESCRIPTION OF EMBODIMENTS

Figure 1:
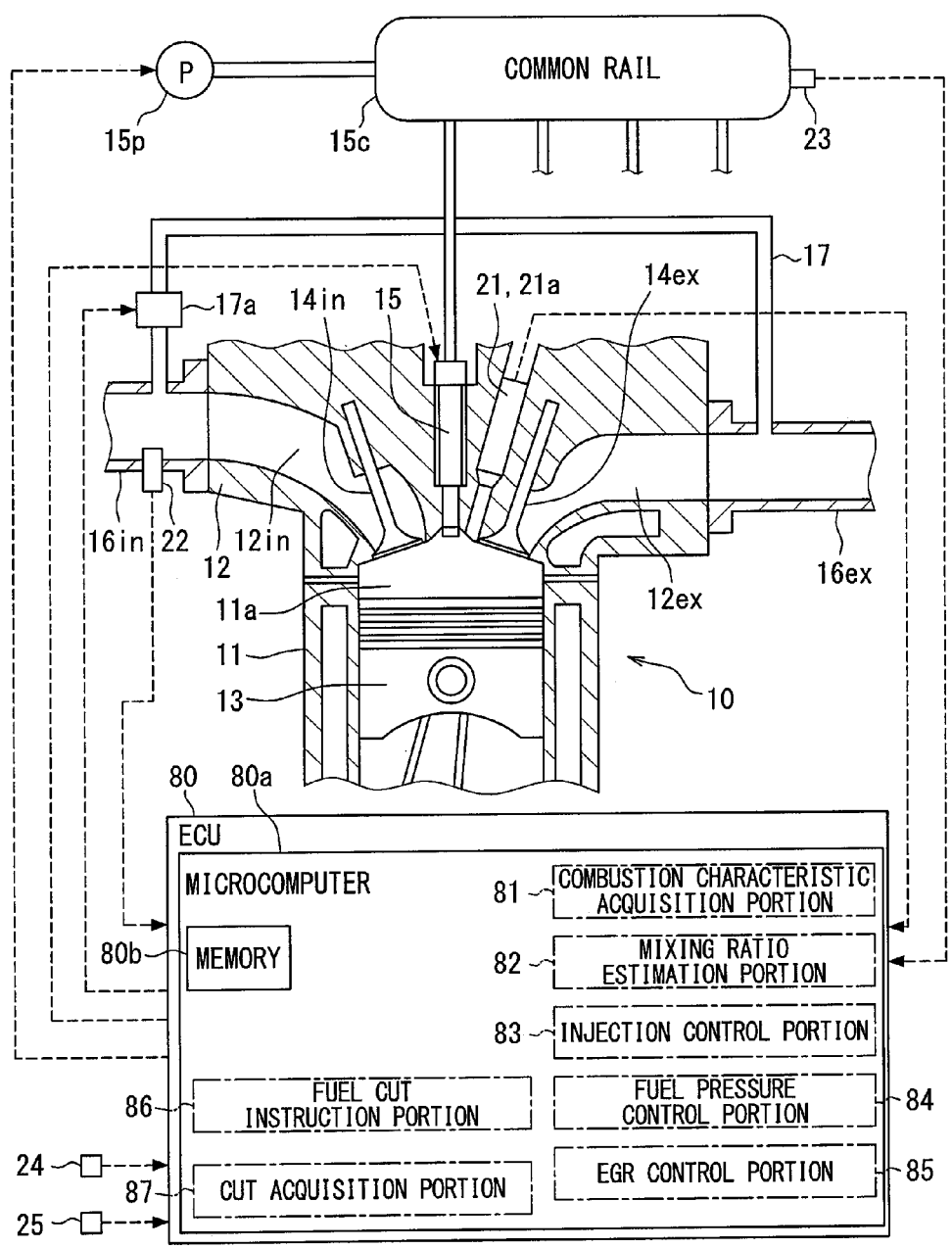
FIG. 1 is a diagram showing a fuel estimation apparatus according to an embodiment of the present disclosure, and a combustion system of an internal combustion engine to which the fuel estimation apparatus is applied.

Embodiments of the present disclosure will be described hereafter referring to drawings. In the embodiments, a part that corresponds to a matter described in a preceding embodiment may be assigned with the same reference numeral, and redundant explanation for the part may be omitted. When only a part of a configuration is described in an embodiment, another preceding embodiment may be applied to the other parts of the configuration. The parts may be combined even if it is not explicitly described that the parts can be combined. The embodiments may be partially combined even if it is not explicitly described that the embodiments can be combined, provided there is no harm in the combination.

According to an embodiment of the present disclosure, a fuel estimation apparatus is constituted based on an electric control unit (ECU) 80 shown in FIG. 1. The ECU 80 includes a microcomputer 80a and a memory 80b. The microcomputer 80a executes a specified program so as to control operations of a fuel injector 15, a fuel pump 15$p$, and an exhaust gas recirculation (EGR) valve 17$a$ which are included in an internal combustion engine 10. A combustion state of a fuel generated in a combustion chamber 11$a$ of the internal combustion engine 10 is controlled in a required state by the above controls. The internal combustion engine 10 and the ECU 80 are mounted to a vehicle, and the vehicle travels by using an output of the internal combustion engine 10 as a driving source.

The internal combustion engine 10 includes a cylinder block 11, a cylinder head 12, a piston 13, an intake valve 14in, an exhaust valve 14ex, and the fuel injector 15. The fuel pump 15$p$ presses and feeds the fuel in a fuel tank to a common rail 15$c$. Since the ECU 80 controls the operation of the fuel pump 15$p$, the fuel is accumulated in the common rail 15$c$ in a state where a pressure of the fuel is maintained to be a target pressure Ptrg. The common rail 15$c$ distributes the fuel that is accumulated to the fuel injector 15 in each cylinder.

The fuel injector 15 is mounted to the cylinder head 12. The fuel injected from the fuel injector 15 is mixed with an intake gas to be a mixing gas in the combustion chamber 11$a$. The mixing gas is compressed by the piston 13 to be self-ignited. The internal combustion engine 10 is a diesel engine of a compression self-ignition type, and a light oil is used as the fuel.

The fuel injector 15 includes a body receiving an electromagnetic actuator and a valve member. When the ECU 80 controls to turn on the electromagnetic actuator, a leakage passage of a back-pressure chamber that is not shown is opened according to an electromagnetic attractive force, the valve member is opened according to a decreasing of a back pressure, an injection port arranged in the body is opened, and the fuel is injected from the injection port. When the ECU 80 controls to turn off the electromagnetic actuator, the valve member is closed, and a fuel injection is stopped.

An intake port 12in and an exhaust port 12ex which are arranged in the cylinder head 12 are connected with an intake pipe 16in and an exhaust pipe 16ex, respectively. The intake pipe 16in and the exhaust pipe 16ex are connected with an EGR pipe 17, and a part of an exhaust gas which is an EGR gas is introduced (returned) into the intake pipe 16in through the EGR pipe 17. The EGR pipe 17 is provided with the EGR valve 17$a$. Since the ECU 80 controls the operation of the EGR valve 17$a$, an opening degree of the EGR pipe 17 is controlled, and a flow rate of the EGR gas is controlled.

The ECU 80 receives detection signals from various sensors including a cylinder pressure sensor 21, an oxygen concentration sensor 22, a common-rail pressure sensor 23, a crank angle sensor 24, and an accelerator pedal sensor 25.

The cylinder pressure sensor 21 is mounted to the cylinder head 12 and outputs the detection signal depending on a cylinder pressure that is a pressure in the combustion chamber 11$a$. The cylinder pressure sensor 21 includes a temperature detection element 21$a$ besides a pressure detection element. The cylinder pressure sensor 21 outputs the detection signal depending on a cylinder temperature that is a temperature in the combustion chamber 11$a$. The oxygen concentration sensor 22 is mounted to the intake pipe 16in, and outputs the detection signal depending on a concentration of an oxygen in the intake gas. The intake gas that is a detection target includes the fresh air and the EGR gas. The common-rail pressure sensor 23 is mounted to the common rail 15$c$, and outputs the detection signal depending on a pressure of the fuel accumulated in the common rail 15$c$. In this case, the pressure of the fuel accumulated in the common rail 15$c$ is referred to as a common-rail pressure.

The crank angle sensor 24 outputs the detection signal depending on a rotational speed of a crank shaft that is rotatably driven by the piston 13. In this case, the rotational speed is equivalent to an engine speed. The accelerator pedal sensor 25 outputs the detection signal depending on a pressing position of an accelerator pedal which is operated by a driver of the vehicle. In this case, the pressing position of the accelerator pedal is equivalent to an engine load.

The ECU 80 controls the operations of the fuel injector 15, the fuel pump 15$p$, and the EGR valve 17$a$, based on the detection signals. Therefore, the ECU 80 controls an injection start time point of the fuel, an injection amount of the fuel, an injection pressure of the fuel, and a flowing amount of the EGR gas. The microcomputer 80$a$ of when controlling the operation of the fuel injector 15 is equivalent to an injection control portion 83 to control the injection start time point of the fuel, the injection amount of fuel, and an injection number of a multiple injection. The microcomputer 80$a$ of when controlling the operation of the fuel pump 15$p$ equivalent to a fuel pressure control portion 84 to control the injection pressure. The microcomputer 80$a$ of when controlling the operation of the EGR valve 17$a$ equivalent to an EGR control portion 85 to control the flowing amount of the EGR gas.

Figure 2:
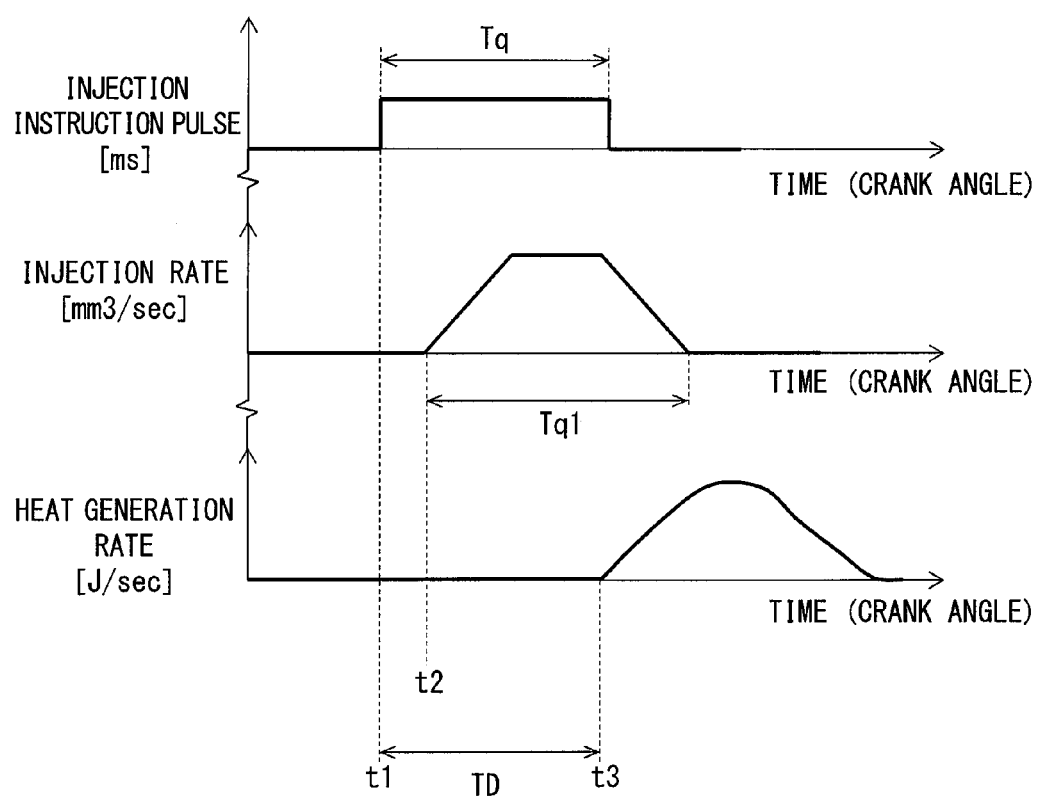
FIG. 2 is a diagram showing an ignition delay time.

The microcomputer 80$a$ also functions as a combustion characteristic acquisition portion 81 to acquire a detection value of a physical amount relating to the combustion. In this case, the detection value of the physical amount relating to the combustion is equivalent to a combustion characteristic value. According to the present embodiment, the combustion characteristic value is the ignition delay time TD shown in FIG. 2. As shown in FIG. 2, an injection instruction pulse indicates a pulse signal that is outputted from the microcomputer 80$a$. An energization of the fuel injector 15 is controlled according to the pulse signal. Specifically, the energization starts at a time point t1 that the injection instruction pulse is turned on, and continues in a pulse on period Tq. In other words, a timing that the injection instruction pulse is turned on controls the injection start time point. Further, the pulse on period T controls an injection time period of the fuel, and then controls the injection amount.

As shown in FIG. 2, an injection rate indicating an injection state of the fuel which is generated by a valve-opening operation and a valve-closing operation that are executed according to the pulse signal is relative to the injection amount. Specifically, an injection rate indicates the injection amount of the fuel injected per unit time. As shown in FIG. 2, a time delay exists between the time point t1 that the energization starts and a time point t2 that the injection is actually started. Further, a time delay exists between an energization complete time point and a time point that the injection is actually stopped. The pulse on period Tq controls an actual injection period Tq1.

As shown in FIG. 2, a heat generation rate indicates the combustion state of the fuel injected in the combustion chamber 11$a$. Specifically, the heat generation rate indicates a heat amount where the mixing gas including the fuel and the intake gas is self-ignited per unit time. As shown in FIG. 2, a time delay exists between the time point t2 that the injection is actually started and a time point t3 that the combustion is actually started. According to the present embodiment, a time period from the time point t1 to the time point t3 is referred to as the ignition delay time TD.

The combustion characteristic acquisition portion 81 estimates the time point t3, based on a variation of the cylinder pressure detected by the cylinder pressure sensor 21. Specifically, in a time period from a time point that the piston 13 reaches a top dead center to a time point that a crank angle rotates by a predetermined value, the combustion characteristic acquisition portion 81 estimates a time point that the cylinder pressure rapidly increases as the combustion start time point that is the time point t3. The combustion characteristic acquisition portion 81 calculates the ignition delay time TD based on an estimation result. Further, the combustion characteristic acquisition portion 81 acquires various states in the combustion every time the combustion occurs. In this case, various states include combustion conditions. Specifically, the combustion characteristic acquisition portion 81 acquires the cylinder pressure, the cylinder temperature, an intake-gas oxygen concentration, and the injection pressure, as the combustion conditions. In this case, the intake-gas oxygen concentration is the concentration of the oxygen in the intake gas.

The combustion conditions are equivalent to combustion parameters indicating easiness levels of the combustions. When the cylinder pressure right before the combustion occurs is higher and when the cylinder temperature right before the combustion occurs is higher and when intake-gas oxygen concentration is higher and when the injection pressure is higher, the mixing gas becomes more easily self-ignited. The cylinder pressure and the cylinder temperature which are detected at the time point t1 that the energization of the fuel injector 15 starts may be used as the cylinder pressure right before the combustion occurs and the cylinder temperature right before the combustion occurs, respectively. The cylinder pressure is detected by the cylinder pressure sensor 21, the cylinder temperature is detected by the temperature detection element 21a, the intake-gas oxygen concentration is detected by the oxygen concentration sensor 22, and the injection pressure is detected by the common-rail pressure sensor 23. The combustion characteristic acquisition portion 81 stores the ignition delay time TD in association with the combustion conditions correlative to the combustion used to estimate the ignition delay time, in the memory 80b.

The microcomputer 80a also functions as a mixing ratio estimation portion 82 to estimate mixing ratios of various components included in the fuel, based on plural combustion characteristics detected in different combustion conditions. For example, the microcomputer 80a calculates mixing amounts of various components by substituting the ignition delay times TD in different combustion conditions for those in an equation shown in FIG. 3. The microcomputer 80a calculates the mixing ratios of various components by dividing a total sum of the mixing amounts by each of the mixing amounts.

As shown in FIG. 3, a molecular structure type is constituted by values arranged in a matrix including x+1 rows and 1 column. The values indicate the mixing amounts of various components. The various components are components divided by types of a molecular structure. The types of the molecular structure include a normal paraffin type, an isoparaffin type, a naphthenic type, and an aromatic type.

As shown in FIG. 3, a constant is constituted by values arranged in a matrix including x+1 rows and y+1 columns. The values are constants established based on a pretest. As shown in FIG. 3, the combustion parameters are constituted by values arranged in a matrix including y+1 rows and 1 column. The values are the ignition delay time TD acquired by the combustion characteristic acquisition portion 81. For example, the value arranged at 1st row and 1st column is the ignition delay time TD(i) that is acquired in a combustion condition i that is a specified combination of the parameters, and the value arranged at 2nd row and 1st column is the ignition delay time TD(j) that is acquired in a combustion condition j. The combustion condition i and the combustion condition j are set based on values different in all of the parameters. Further, as shown in FIG. 3, P(i), T(i), $O_2(i)$, Pc(i) indicate the cylinder pressure, the cylinder temperature, the intake-gas oxygen concentration, and the injection pressure which are correlative to the combustion condition i, respectively. Similarly, P(j), T(j), $O_2(j)$, Pc(j) indicate the cylinder pressure, the cylinder temperature, the intake-gas oxygen concentration, and the injection pressure which are correlative to the combustion condition j, respectively.

Hereafter, referring FIGS. 4 to 6, a calculation of the molecular structure type will be described.

As shown in FIG. 4, since the mixing gas becomes more easily self-ignited when the cylinder oxygen concentration that is the concentration of the oxygen included in the mixing gas in the combustion becomes higher, the ignition delay time TD becomes shorter. Solid lines L1, L2, and L3 are characteristic lines indicating relationships between the cylinder oxygen concentrations and the ignition delay times TD. The characteristic lines are different according to the fuel. Specifically, the characteristic lines are different according to the mixing ratios of the molecular structure types included in the fuel. Therefore, when the combustion characteristic acquisition portion 81 detects the ignition delay time TD of when the cylinder oxygen concentration is $O_2(i)$, the combustion characteristic acquisition portion 81 can estimate one of the molecular structure types. When the combustion characteristic acquisition portion 81 compares the ignition delay time TD of when the cylinder oxygen concentration is $O_2(i)$ with the ignition delay time TD of when the cylinder oxygen concentration is $O_2(j)$, the combustion characteristic acquisition portion 81 can estimate the mixing ratio with a higher accuracy. As shown in FIG. 4, the solid line L1 is the characteristic line obtained according to a fuel F1, the solid line L2 is the characteristic line obtained according to a fuel F2, and the solid line L3 is the characteristic line obtained according to a fuel F3.

Similarly, as shown in FIG. 5, since the mixing gas becomes more easily self-ignited when the cylinder temperature becomes higher, the ignition delay time TD becomes shorter. Solid lines LL1, LL2, and LL3 are characteristic lines indicating relationships between the cylinder temperatures and the ignition delay times TD. The characteristic lines are different according to the fuel. Specifically, the characteristic lines are different according to the mixing ratios of the molecular structure types included in the fuel. Therefore, when the combustion characteristic acquisition portion 81 detects the ignition delay time TD of when the cylinder temperature is T(i), the combustion characteristic acquisition portion 81 can estimate one of the molecular structure types. When the combustion characteristic acquisition portion 81 compares the ignition delay time TD of when the cylinder temperature is T(i) with the ignition delay time TD of when the cylinder temperature is T(j), the combustion characteristic acquisition portion 81 can estimate the mixing ratio with a higher accuracy. As shown in FIG. 5, the solid line LL1 is the characteristic line obtained according to the fuel F1, the solid line LL2 is the characteristic line obtained according to the fuel F2, and the solid line LL3 is the characteristic line obtained according to the fuel F3.

The molecular structure type highly affecting the characteristic line correlative to the cylinder oxygen concentration as shown in FIG. 4 is different from the molecular structure type highly affecting the characteristic line correlative to the cylinder temperature as shown in FIG. 5. As the above description, the molecular structure types highly affecting the characteristic lines are different in plural combustion conditions which are correlative to the characteristic line. Therefore, the combustion characteristic acquisition portion 81 can estimate the mixing ratio of the molecular structure type which is large or small as shown in FIG. 6, based on combinations of the ignition delay times TD acquired in different parameters (different combustion conditions).

As shown in FIG. 6, a molecular structure type A is the molecular structure type highly affecting the characteristic line correlative to the cylinder oxygen concentration. In this case, the characteristic line is referred to as a first characteristic line, and the cylinder oxygen concentration is referred to as a first parameter. Further, a molecular structure type B is the molecular structure type highly affecting the characteristic line correlative to the cylinder temperature. In this case, the characteristic line is referred to as a second characteristic line, and the cylinder temperature is referred to as a second parameter. Furthermore, a molecular structure type C is the molecular structure type highly affecting the characteristic line correlative to a third parameter. In this case, the characteristic line is referred to as a third characteristic line. When a variation of the ignition delay time TD becomes larger relative to a variation of the first parameter, the mixing of the molecular structure type A included in the mixing gas becomes higher. Similarly, when the variation of the ignition delay time TD becomes larger relative to a variation of the second parameter, the mixing of the molecular structure type B included in the mixing gas becomes higher. Further, when the variation of the ignition delay time TD becomes larger relative to a variation of the third parameter, the mixing of the molecular structure type C included in the mixing gas becomes higher. Thus, the combustion characteristic acquisition portion 81 can estimate the mixing ratio of the molecular structure type A, the molecular structure type B, and the molecular structure type C, relative to the fuel F1, the fuel F2, and the fuel F3, respectively.

Figure 7:
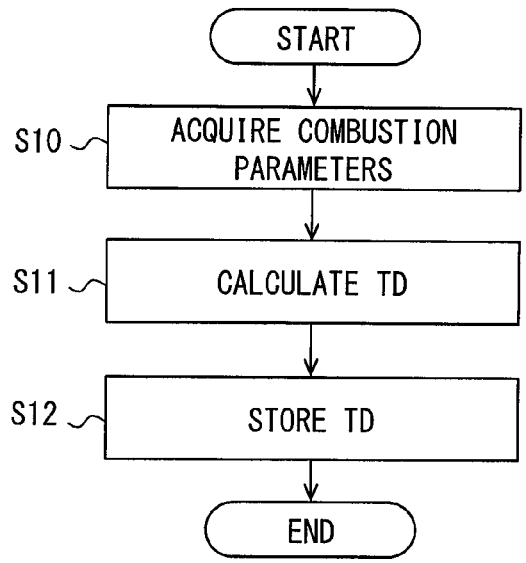
FIG. 7 is a flowchart showing a processing flow of a microcomputer which is a storing flow of an ignition delay time.

FIG. 7 is a flowchart showing a processing flow of a program executed by the combustion characteristic acquisition portion 81. The processing flow is executed every time that a pilot injection is instructed. In one combustion cycle, it is possible that an injection control executes the multiple injection where the same fuel injector 15 is controlled to inject the fuel for plural times. In the multiple injection, an injection that injects the injection amount with a maximum value is referred to as a main injection, and an injection executed right before the main injection is referred to as the pilot injection.

First, at S10 in FIG. 7, the combustion characteristic acquisition portion 81 acquires the parameters. Next, at S11, the combustion characteristic acquisition portion 81 estimates the time point t3 that is the combustion start time point based on a detection value of the cylinder pressure sensor 21, and calculates the ignition delay time TD correlative to the pilot injection. Next, at S12, the combustion characteristic acquisition portion 81 stores the ignition delay time TD calculated at S11 in association with the combustion condition that is equivalent to the parameters acquired at S10, in the memory 80b.

Specifically, a value range where the parameters can be obtained is previously divided into plural regions, and combinations of regions of plural parameters are previously established. As shown in FIG. 3, the ignition delay time TD(i) indicates the ignition delay time TD acquired in a case where regions of P(i), T(i), $O_2(i)$, and Pc(i) are combined. Similarly, the ignition delay time TD(j) indicates the ignition delay time TD acquired in a case where regions of P(j), T(j), $O_2(j)$, and Pc(j) are combined. At S12, the combustion characteristic acquisition portion 81 determines whether a combustion condition that is a combination of plural parameters acquired at S10 is equivalent to one of the combustion conditions which are combinations that are previously established. Then, the combustion characteristic acquisition portion 81 stores the ignition delay time TD calculated at S11, as the ignition delay time TD that corresponds to the combustion condition. In other words, the combustion characteristic acquisition portion 81 stores the ignition delay time TD in association with the combustion condition.

It is possible that none of the combustion conditions which are previously established is equivalent to the combustion condition acquired at S10. In this case, the combustion characteristic acquisition portion 81 terminates the processing flow shown in FIG. 7, without storing the ignition delay time TD in the memory 80b. When the ignition delay time TD correlative to the combustion condition that is equivalent to the combustion condition acquired at S10 has been stored in the memory 80b, the combustion characteristic acquisition portion 81 updates the ignition delay time TD in the memory 80b by storing the ignition delay time TD that is calculated at S11 in the memory 80b.

Figure 8:
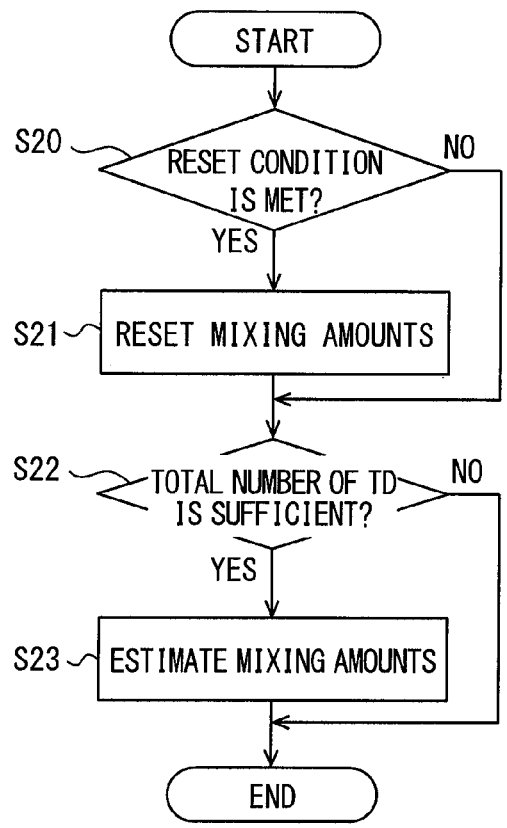
FIG. 8 is a flowchart showing a processing flow of the microcomputer which is a estimation flow of a mixing ratio of each of a molecular structure type.

FIG. 8 is a flowchart showing a processing flow of a program executed by the mixing ratio estimation portion 82. The above processing flow is repeatedly executed at a predetermined period, in an operation time period of the internal combustion engine 10. First, at S20 in FIG. 8, when it is highly possible that the fuel stored in the fuel tank is mixed with other fuel in a case where a user supplies a fuel into the fuel tank, the mixing ratio estimation portion 82 determines that the mixing ratios of the molecular structure types change and a reset condition is met. For example, when an increasing of a fuel surplus amount is detected by a sensor detecting the fuel surplus amount in the fuel tank in a case where the internal combustion engine 10 is stopped, the mixing ratio estimation portion 82 determines that the reset condition is met.

When the mixing ratio estimation portion 82 determines that the reset condition is met, the mixing ratio estimation portion 82 proceeds to S21. At S21, the mixing ratio estimation portion 82 resets values of the mixing amounts which are estimated. In the above reset operation, the mixing ratio estimation portion 82 resets the mixing amounts which are latest and are estimated at S23, and resets values of the ignition delay time TD stored according to the processing flow shown in FIG. 7. Thus, in a time period from a time point that a previous reset condition that is the reset condition used as a reference condition is met to a time point that a later reset condition that is the reset condition met right after the reference condition is met, the ignition delay time TD is continuously accumulated (added or sampled) in the memory 80b.

At S22, the mixing ratio estimation portion 82 determines whether a sampling number that is a total number of the ignition delay times TD stored in the memory 80b is sufficient to estimate the mixing ratios of the molecular structure type. Specifically, when the sampling number is greater than or equal to a predetermined value, the mixing ratio estimation portion 82 determines that the sampling number is sufficient. Alternatively, when the ignition delay times TD relative to plural combustion conditions that are predetermined established among the combustion conditions equivalent to combinations of regions that are storage objects are stored, the mixing ratio estimation portion 82 determines that the sampling number is sufficient.

When the mixing ratio estimation portion 82 determines that the sampling number is sufficient, the mixing ratio estimation portion 82 proceeds to S23. At S23, the mixing ratio estimation portion 82 calculates the mixing amount of each of the molecular structure types, by substituting the ignition delay times TD that are sampled for those in the equation shown in FIG. 3. The combustion characteristic acquisition portion 81 changes a row number of the constant according to a sampling number that is a row number of the combustion parameters. Alternatively, when the ignition delay time TD is not acquired, the combustion characteristic acquisition portion 81 substitutes nominal values for the ignition delay times TD in the equation shown in FIG. 3. The combustion characteristic acquisition portion 81 calculates the mixing ratio of each of the molecular structure types, based on the mixing amount of each of the molecular structure types which is calculated.

As the above description, the microcomputer 80a functions as the injection control portion 83, the fuel pressure control portion 84, and the EGR control portion 85.

The injection control portion 83 controls the injection start time point, the injection amount, and the injection number, by setting the pulse signal shown in FIG. 2, so as to control the injection start time point, the injection amount, and the injection number to be target values. In this case, the injection control portion 83 executes the injection control. The injection number is the injection number of the multiple injection.

The fuel pressure control portion 84 controls an operation of a regulating valve that controls a flow rate of the fuel suctioned in the fuel pump 15p. Specifically, the fuel pressure control portion 84 feedback controls the operation of the regulating valve, based on a difference between an actual common-rail pressure detected by the common-rail pressure sensor 23 and the target pressure Ptrg that is a target value. Then, the fuel pressure control portion 84 controls a discharge amount of the fuel pump 15p per unit time, and controls the actual common-rail pressure to be the target value. In this case, the fuel pressure control portion 84 executes a fuel pressure control. The EGR control portion 85 controls a valve opening degree of the EGR valve 17a to control the EGR amount to be the target value. In this case, the EGR control portion 85 executes an EGR control.

The microcomputer 80a also functions as a fuel cut instruction portion 86 and a cut acquisition portion 87.

When a predetermined condition is met during an operation of the internal combustion engine 10, the fuel cut instruction portion 86 instructs to temporarily stop an injection of the fuel so as to improve the fuel consumption. In this case, the injection of the fuel is equivalent to the fuel injection. Specifically, when the engine speed is greater than or equal to a predetermined speed that is set to be greater than or equal to an idling-reduction rotation speed and when an accelerator pressing amount is zero, it is determined that the predetermined condition is met. For example, when the vehicle is travelling in a case where an engine brake functions, the predetermined condition is met, and the injection of the fuel is temporarily stopped according to a fuel cut instruction.

During a fuel cut instruction period that the fuel cut instruction portion 86 instructs a fuel cut, the cut acquisition portion 87 controls the operation of the internal combustion engine 10 to control the combustion at a required combustion condition. In this case, the combustion is referred to as a learning combustion. The required combustion condition is set to be the combustion condition of regions where the ignition delay time TD has not been acquired. A fuel injection amount of the learning combustion is set to a slight amount that vehicle passengers cannot feel a torque variation generated according to the learning combustion. The injection number of the learning combustion is set to one. In the learning combustion, similarly to the combustion characteristic acquisition portion 81, the cut acquisition portion 87 acquires the combustion characteristic value that is the ignition delay time TD and the combustion condition that is equivalent to the parameters, and stores the combustion characteristic value in association with the combustion condition in the memory 80b.

Figure 9:
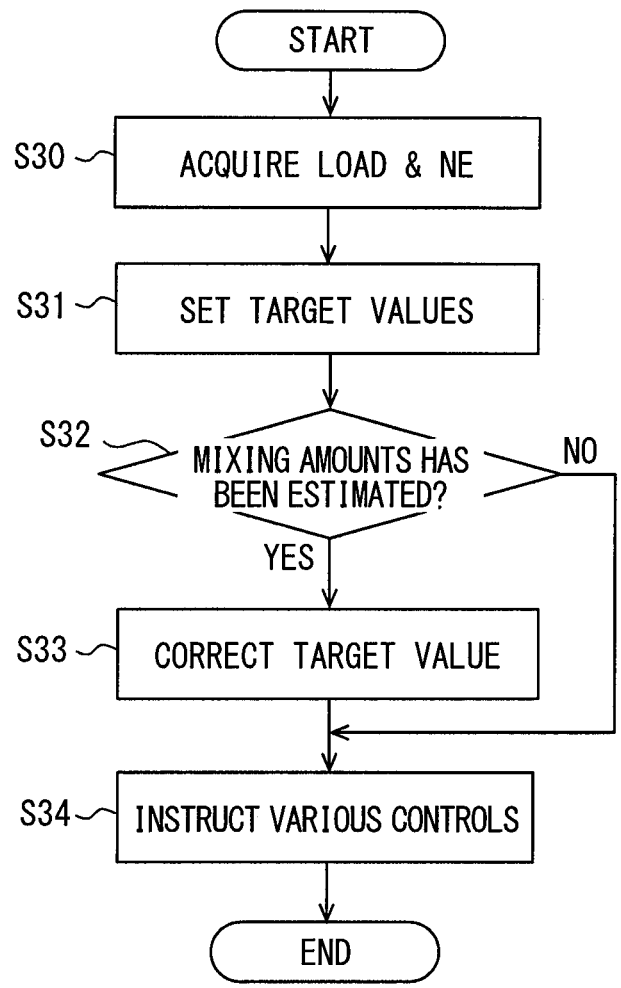
FIG. 9 is a flowchart showing a processing flow of the microcomputer which is a control flow of a combustion system.

FIG. 9 is a flowchart showing a processing flow of a program executed by the injection control portion 83, the fuel pressure control portion 84, and the EGR control portion 85. The above processing flow is repeatedly executed at a predetermined period, in an operation time period of the internal combustion engine 10. First, at S30 in FIG. 9, the microcomputer 80a acquires the engine speed (NE), the engine load, and an engine coolant temperature that is a temperature of a coolant of the internal combustion engine 10. At S31, the microcomputer 80a sets the target values correlative to the injection control executed by the injection control portion 83, the fuel pressure control executed by the fuel pressure control portion 84, and the EGR control executed by the EGR control portion 85, based on the values acquired at S30.

At S32, the microcomputer 80a determines whether the mixing ratio of each of the molecular structure types is estimated in the processing flow in FIG. 8 without being reset. When the microcomputer 80a determines that the mixing ratio is estimated, the microcomputer 80a proceeds to S33. At S33, the microcomputer 80a corrects the target values set at S31 according to the mixing ratio. For example, the microcomputer 80a corrects at least one of the target values, according to one of the fuels F1, F2, and F3 shown in FIG. 6. At S34, the injection control portion 83 outputs an instruction signal to execute the injection control, the fuel pressure control portion 84 outputs an instruction signal to execute the fuel pressure control, and the EGR control portion 85 outputs an instruction signal to execute the EGR control, according to the target values set at S31 or the target values that are corrected at S33.

As the above description, according to the present embodiment, the fuel estimation apparatus that is equivalent to the ECU 80 includes the combustion characteristic acquisition portion 81 and the mixing ratio estimation portion 82. The combustion characteristic acquisition portion 81 acquires the detection value of the physical amount relating to the combustion of the internal combustion engine 10, as the combustion characteristic. The mixing ratio estimation portion 82 estimates the mixing ratios of the various components included in the fuel, based on plural combustion characteristics detected in different combustion conditions.

When fuels used in the combustion are the same and when the combustion conditions such as the cylinder pressures or the cylinder temperatures are different from each other, the combustion characteristic values such as the ignition delay times or the heat generation amounts differ. For example, as shown in FIG. 4, regarding the fuel F1, the combustion characteristic value that is the ignition delay time TD decreases in accordance with the combustion condition where the cylinder oxygen concentration increases. The solid lines as shown in FIG. 4 which are characteristic lines indicating levels of variations of the combustion characteristic values relative to variations of the combustion conditions differ in the fuels F1, F2, and F3 that are different from each other in the mixing ratios of the molecular structure types. According to the present embodiment, since the microcomputer 80*a* estimates the mixing ratios of the molecular structure types included in the fuel based on the combustion characteristic values that are the ignition delay times TD detected in different combustion conditions, the microcomputer 80*a* can further accurately acquire the fuel characteristic that is a characteristic of the fuel.

According to the present embodiment, the component that is an estimation object of the mixing ratio is a component that is divided by types of the molecular structure. When the cetane numbers of the fuels are the same and when the mixing ratios of various components included in the fuels are different from each other, the characteristic line of the ignition delay time TD (combustion characteristic value) shown in FIGS. 4 and 5 differs. According to the present embodiment where the mixing ratios are considered in the injection control, in the fuel pressure control, and in the EGR control, the fuel estimation apparatus can more accurately control the combustion in the combustion state that is required than that according to a configuration where the cetane number or the fuel density is considered in the above controls.

According to the present embodiment, the types of the molecular structure include at least one of a normal paraffin type, an isoparaffin type, a naphthenic type, or an aromatic type. In other words, the types of the molecular structure include one or more of the normal paraffin type, the isoparaffin type, the naphthenic type, and the aromatic type. Since the above types of the molecular structure highly affect the combustion state, an estimation of the mixing ratios of the components divided according to the above types is used to consider the mixing ratios in the controls correlative to the combustion.

According to the present embodiment, the combustion condition is a condition specified by a combination of parameters of plural types. In other words, the microcomputer 80*a* acquires the combustion characteristic value in the combustion where the value of the parameter differs, for each of the parameters. Thus, the microcomputer 80*a* acquires the combustion characteristic value in the combustion where the value of the parameter differs for the parameter of the same type, and the microcomputer 80*a* can more accurately estimate the mixing ratios than that in a configuration where the mixing ratios are estimates based on the combustion conditions and the combustion characteristic values.

According to the present embodiment, the parameters of plural types correlative to the combustion conditions include at least one of the cylinder pressure, the cylinder temperature, the intake-gas oxygen concentration, or the injection pressure. In other words, the parameters include one or more of the cylinder pressure, the cylinder temperature, the intake-gas oxygen concentration, and the injection pressure. Since the parameters highly affect the combustion state, the microcomputer 80*a* can accurately estimate the mixing ratios by using the combustion characteristic values in the combustion where the combustion conditions differ.

According to the present embodiment, the combustion characteristic value is the ignition delay time TD from a time point that the fuel injection is instructed to a time point that the fuel is self-ignited. Since the ignition delay time TD is highly affected by the mixing ratios of various components, the microcomputer 80*a* can accurately estimate the mixing ratios based on the ignition delay time TD.

According to the present embodiment, the combustion characteristic acquisition portion 81 acquires the combustion characteristic value correlative to the combustion of the fuel injected before the main injection. In other words, the combustion characteristic acquisition portion 81 acquires the combustion characteristic value correlative to the combustion of the fuel injected in the pilot injection. Since the cylinder temperature becomes higher when the fuel in the main injection combusts, the fuel after the main injection becomes more easily to combust. In this case, the fuel after the main injection becomes more easily self-ignited. Thus, it is difficult that a variation of the combustion characteristic value is generated due to a difference in the mixing ratio of the fuel. Since the fuel injected before the main injection is not affected by a main combustion, it is likely that the variation of the combustion characteristic value is generated due to the difference in the mixing ratio of the fuel. An estimation accuracy of the mixing ratios can be improved by estimating the mixing ratios based on the combustion characteristic value.

According to the present embodiment, the fuel estimation apparatus includes the fuel cut instruction portion 86 and the cut acquisition portion 87. When the predetermined condition is met during the operation of the internal combustion engine 10, the fuel cut instruction portion 86 instructs to temporarily stop the injection of the fuel. During the fuel cut instruction period that the fuel cut instruction portion 86 instructs the fuel cut, the cut acquisition portion 87 acquires the combustion characteristic value in the combustion condition that is required. Therefore, since the learning combustion is executed in the combustion condition of regions where the ignition delay time TD has not been acquired, the sampling number that is the total number of the ignition delay times TD accumulated to be sufficient to estimate the mixing ratios of the molecular structure types. Then, a time period of an accumulation of the total number can be shortened. Thus, it can be achieved in an early stage that the mixing ratios are considered to a control of the internal combustion engine 10.

(Other Embodiment)

The present disclosure is not limited to the embodiments mentioned above, and can be applied to various embodiments as followings. Further, it is to be understood that the disclosure is not limited to the embodiments and constructions. The present disclosure is intended to cover various modification and equivalent arrangements. In addition, while the various combinations and configurations, which are preferred, other combinations and configurations, including more, less or only a single element, are also within the spirit and scope of the present disclosure.

According to the above embodiments, as shown in FIG. 2, a time period from the time point t1 that the energization starts to the time point t3 that the combustion starts is defined as the ignition delay time TD. However, a time period from the time point t2 that the injection is started to the time point t3 that the combustion starts may be defined as the ignition delay time TD. The combustion system controller may detect a time point that a variation is generated in the fuel pressure including the common rail pressure when the injection is started and estimate the time point t2 that the injection is started based on the above detection time point.

As shown in FIG. 1, the combustion characteristic acquisition portion 81 acquires the ignition delay time TD as the detection value of the physical amount relating to the combustion. In this case, the detection value of the physical amount relating to the combustion is equivalent to the combustion characteristic value. However, the combustion system controller may acquire a waveform indicating a variation of the heat generation rate or acquire the heat generation amount that is an amount of the heat generated in the combustion of the fuel, as the combustion characteristic value. Further, the combustion system controller may estimate the mixing ratios of the various components based on plural types of the combustion characteristic values such as the ignition delay time TD, the waveform of the heat generation rate, and the heat generation amount. For example, the values of the constant shown in FIG. 3 may be set to values correlative to the plural types of the combustion characteristic values, and the combustion system controller may estimate the mixing ratios by substituting the plural types of the combustion characteristic values for the combustion parameters shown in FIG. 3.

As shown in FIG. 3, the combustion conditions are set such that all of the ignition delay times TD are different from each other. In other words, in combustion conditions i, j, k, and l which are specified combinations of the parameters, the cylinder pressures are all set to different values P(i), P(j), P(k), and P(l), respectively. Similarly, the cylinder temperatures T, the intake-gas oxygen concentrations O2, and the injection pressures Pc are also set to different values. However, the combustion system controller may set as least one of the parameters to be different from other parameters, for the different combustion conditions. For example, in the combustion conditions i and j, the combustion system controller may set the cylinder temperatures T, the intake-gas oxygen concentrations O2, and the injection pressures Pc to be the same values, respectively, and set the cylinder pressures to be P(i) and P(j) which are different from each other.

As shown in FIG. 3, the combustion system controller sets plural combustion conditions specified by combinations of plural types of the parameters and acquires the combustion characteristic values of when the fuel combusts in the plural combustion conditions. However, the combustion controller may set one type of the parameters and acquire the combustion characteristic values of when the fuel combusts in the combustion condition where the value of the parameter differs.

Alternatively, the combustion controller may change an injection time point to a time point (crank angle) that the cylinder temperature becomes a request value and positively acquire the combustion characteristic value in the combustion condition that is required. It is preferable that the injection time point is changed in one or more specified cylinders without changing the injection time point in all the cylinders. It is preferable that the change of the injection time point is prohibited in the main injection. Further, it is preferable that the change of the injection time point is prohibited in the pilot injection that highly affects the main injection. Furthermore, an exclusive injection that is used to detect the combustion characteristic value may be added, and the combustion system controller may acquire the combustion characteristic value of when the fuel combusts in the exclusive injection in the required state.

According to the above embodiments, the combustion system controller acquires the combustion characteristic value correlative to the combustion of the fuel injected right before the main injection. In other words, the combustion system controller acquires the combustion characteristic value correlative to the combustion of the fuel injected in the pilot injection. However, the combustion system controller may acquire the combustion characteristic value correlative to the combustion of the fuel injected after the main injection. Specifically, the combustion system controller may acquire the combustion characteristic value correlative to the combustion of the fuel injected in an after injection or a post injection. Moreover, when a multiple injection where the fuel is injected for plural times is executed before the main injection, a first injection of the multiple injection hardly affects the main injection. Therefore, it is preferable that the combustion system controller acquires the combustion characteristic value correlative to the combustion of the fuel injected in the first injection.

According to the above embodiments, the combustion system controller acquires the combustion characteristic value based on the detection value of the cylinder pressure sensor 21. However, in a configuration that the cylinder pressure sensor 21 is not provided, the combustion system controller may estimate the combustion characteristic value based on a rotation variation of a rotation angle sensor. In this case, the rotation variation is a differential value. For example, the combustion system controller may estimate a time point that the differential value exceeds a predetermined threshold due to a pilot combustion as a pilot ignition time point. The combustion system controller can estimate a pilot combustion amount based on a magnitude of the differential value.

According to the first embodiment, as shown in FIG. 1, the cylinder temperature is detected by the temperature detection element 21a. However, the cylinder temperature may be estimated based on the cylinder pressure detected by the cylinder pressure sensor 21. Specifically, the cylinder temperature may be estimated by a calculation of the cylinder pressure, a cylinder capacity, a weight of a gas in the cylinder, and a gas constant.

The ECU 80 that is a controller has functions which can be achieved by a computer that executes a software stored in a memory that is substantial, a software, a hardware, or a combination of the above. For example, when the controller is constituted by a circuit that is a hardware, the circuit may include a digital circuit including plural logic circuit or may include an analog circuit.

While the present disclosure has been described with reference to the embodiments thereof, it is to be understood that the disclosure is not limited to the embodiments and constructions. The present disclosure is intended to cover various modification and equivalent arrangements. In addition, while the various combinations and configurations, which are preferred, other combinations and configurations, including more, less or only a single element, are also within the spirit and scope of the present disclosure.

What is claimed is:

1. A fuel estimation apparatus comprising:
   a combustion characteristic acquisition portion acquiring a combustion characteristic value indicating a parameter relating to a combustion of an internal combustion engine, the combustion characteristic acquisition portion acquiring the combustion characteristic values of the combustions executed in different combustion conditions; and
   a mixing ratio estimation portion estimating mixing ratios of various components included in a fuel, based on the combustion characteristic values acquired by the combustion characteristic acquisition portion.

2. The fuel estimation apparatus according to claim 1, wherein
   the component that is an estimation object of the mixing ratio is a component that is divided by types of a molecular structure.

3. The fuel estimation apparatus according to claim 2, wherein
the types of the molecular structure include at least one of a normal paraffin type, an isoparaffin type, a naphthenic type, or an aromatic type.

4. The fuel estimation apparatus according to claim 1, wherein
the combustion condition is a condition specified by a combination of parameters of plural types.

5. The fuel estimation apparatus according to claim 4, wherein
the parameters of plural types include at least one of a cylinder pressure, a cylinder temperature, an intake-gas oxygen concentration, or an injection pressure.

6. The fuel estimation apparatus according to claim 1, wherein
the internal combustion engine is a compression self-ignition type, and
the combustion characteristic value is a time period from a time point that the fuel is injected into a combustion chamber of the internal combustion engine to a time point that the fuel is self-ignited, or is a time period from a time point that the fuel injection is instructed to the time point that the fuel is self-ignited.

7. The fuel estimation apparatus according to claim 1, wherein
when a multiple injection that the fuel is injected for plural times is executed in one combustion cycle of the internal combustion engine, the combustion characteristic acquisition portion acquires the combustion characteristic value relating to the combustion of the fuel injected before or after a main injection that injects an injection amount with a maximum value.

8. The fuel estimation apparatus according to claim 1, further comprising:
a fuel cut instruction portion instructing to temporarily stop an injection of the fuel in a case where a predetermined condition is met during an operation of the internal combustion engine; and
a cut acquisition portion executing a learning combustion to inject the fuel at a slight amount and controlling the combustion at a required combustion condition during an fuel cut instruction period that the fuel cut instruction portion instructs a fuel cut, and acquiring the combustion characteristic value.

9. A fuel estimation apparatus comprising:
a combustion characteristic acquisition portion acquiring a combustion characteristic value indicating a parameter relating to a combustion of an internal combustion engine, the combustion characteristic acquisition portion acquiring the combustion characteristic values of the combustions executed in different combustion conditions; and
a mixing ratio estimation portion estimating mixing ratios of various components included in a fuel, based on the combustion characteristic values acquired by the combustion characteristic acquisition portion;
the component that is an estimation object of the mixing ratio is a component that is divided by types of a molecular structure, and
the types of the molecular structure include at least two of a normal paraffin type, an isoparaffin type, a naphthenic type, or an aromatic type.

* * * * *